US00PP26198P3

(12) United States Plant Patent
Knoblauch

(10) Patent No.: US PP26,198 P3
(45) Date of Patent: Dec. 8, 2015

(54) ***BEGONIA* PLANT NAMED 'LEMON ROSE'**

(50) Latin Name: *Begonia×tuberhybrida*
Varietal Denomination: Lemon Rose

(71) Applicant: Catherine J. Knoblauch, Whitecourt (CA)

(72) Inventor: Catherine J. Knoblauch, Whitecourt (CA)

( * ) Notice: Subject to any disclaimer, the term of this patent is extended or adjusted under 35 U.S.C. 154(b) by 225 days.

(21) Appl. No.: 13/998,786

(22) Filed: Dec. 5, 2013

(65) Prior Publication Data

US 2015/0163984 P1 Jun. 11, 2015

(51) Int. Cl.
*A01H 5/02* (2006.01)

(52) U.S. Cl.
USPC ..... Plt./348

(58) Field of Classification Search
USPC ..... Plt./343, 344, 346, 348
See application file for complete search history.

*Primary Examiner* — Susan McCormick Ewoldt
*Assistant Examiner* — Karen Redden
(74) *Attorney, Agent, or Firm* — Barbara Campbell; Bethany R. Roahrig; Cochran Freund & Young, LLC

(57) ABSTRACT

A new cultivar of *Begonia* plant named 'Lemon Rose' that is characterized by compact rounded symmetrical habit, double flowers that are soft lemon-yellow in color and which develop apple blossom pink tones when exposed to full direct bright sun. 'Lemon Rose' blooms continually from early summer, exhibits dark mahogany foliage and prolific basal and lateral branching, is disclosed.

2 Drawing Sheets

Genus and species: *Begonia×tuberhybrida.*
Denomination: 'Lemon Rose'.

BACKGROUND OF THE VARIETY

The present invention relates to a new and distinct cultivar of tuberous *Begonia* plant, botanically of hybrid origin and known as *Begonia* 'Lemon Rose' and will be referred to hereafter by its cultivar name, 'Lemon Rose'.

The new cultivar was derived from a controlled breeding program conducted by the inventor at the inventor's nursery in Whitecourt, Alberta, Canada. The purpose of the breeding program, which commenced in 2006, is to develop novel selections of *begonia* plants with compact and symmetrical plant habits and which are suitable for container and garden use. The inventor has concentrated on developing *begonia* varieties with attractive dark foliage and contrasting bright flowers which are produced consistently from early summer until fall.

'Lemon Rose' resulted from the controlled pollination in 2009 of two unnamed and unreleased seedlings which the inventor had raised and retained from previous cycles in the breeding program. 'Lemon Rose' was selected by the inventor in 2010 for its combination of soft yellow flowers and dark mahogany foliage.

The inventor first asexually reproduced 'Lemon Rose' in 2010 using the method of terminal stem cuttings at the inventor's nursery in Whitecourt, Alberta, Canada. Since that time, the inventor has determined that the characteristics of this cultivar are stable and are reproduced true to type in successive generations via terminal stem cuttings.

SUMMARY

The following traits have been repeatedly observed and represent the characteristics of the new cultivar, which in combination distinguish 'Lemon Rose' as a new and distinct cultivar of *Begonia.*

1. 'Lemon Rose' exhibits a compact rounded symmetrical habit.
2. 'Lemon Rose' achieves a height of 30 cm and a diameter of 20 cm during one growing season in a 1 gallon container.
3. 'Lemon Rose' exhibits double flowers that are soft lemon-yellow in color.
4. The flowers of 'Lemon Rose' develop apple blossom pink tones when exposed to full direct bright sun.
5. 'Lemon Rose' blooms naturally and continually from spring until fall.
6. 'Lemon Rose' exhibits dark mahogany foliage with contrasting emerald green veining.
7. 'Lemon Rose' exhibits prolific basal and lateral branching.
8. 'Lemon Rose' is hardy in USDA zones 9-11.

COMPARISON WITH PARENTS AND CLOSEST KNOWN CULTIVAR

'Lemon Rose' is distinguishable from its parents by flower color. Whereas the flowers of 'Lemon Rose' are soft lemon-yellow in color, the male parent bears white flowers and the female parent bears dark yellow flowers which also are larger than the flowers of 'Lemon Rose'.

The commercial cultivar known to the inventor which most closely resembles 'Lemon Rose' is *Begonia×tuberhybrida* 'Nonstop Yellow' (unpatented). 'Lemon Rose' may be compared with 'Nonstop Yellow' by flower size and flower color. The flowers of 'Lemon Rose' are smaller and lighter in color than the flowers of 'Nonstop Yellow'. In addition, the foliage of 'Lemon Rose' is darker than the foliage of 'Nonstop Yellow'. The inventor considers that 'Lemon Rose' exhibits more prolific basal and lateral branching than is typical for tuberous *begonias* in general.

BRIEF DESCRIPTION OF THE PHOTOGRAPHS

The accompanying colored photographs illustrate the overall appearance and distinct characteristics of the new *Begonia* cultivar 'Lemon Rose' showing the colors as true as it is reasonably possible to obtain in colored reproductions of this type. Colors in the photographs may differ from the color values cited in the detailed botanical description, which accurately describes the actual colors of the new variety of *Begonia* named 'Lemon Rose'.

The photographs were taken in summer 2013 using 14-week-old plants of 'Lemon Rose' which had been grown out of doors in Oxnard, Calif.

Figure 1:
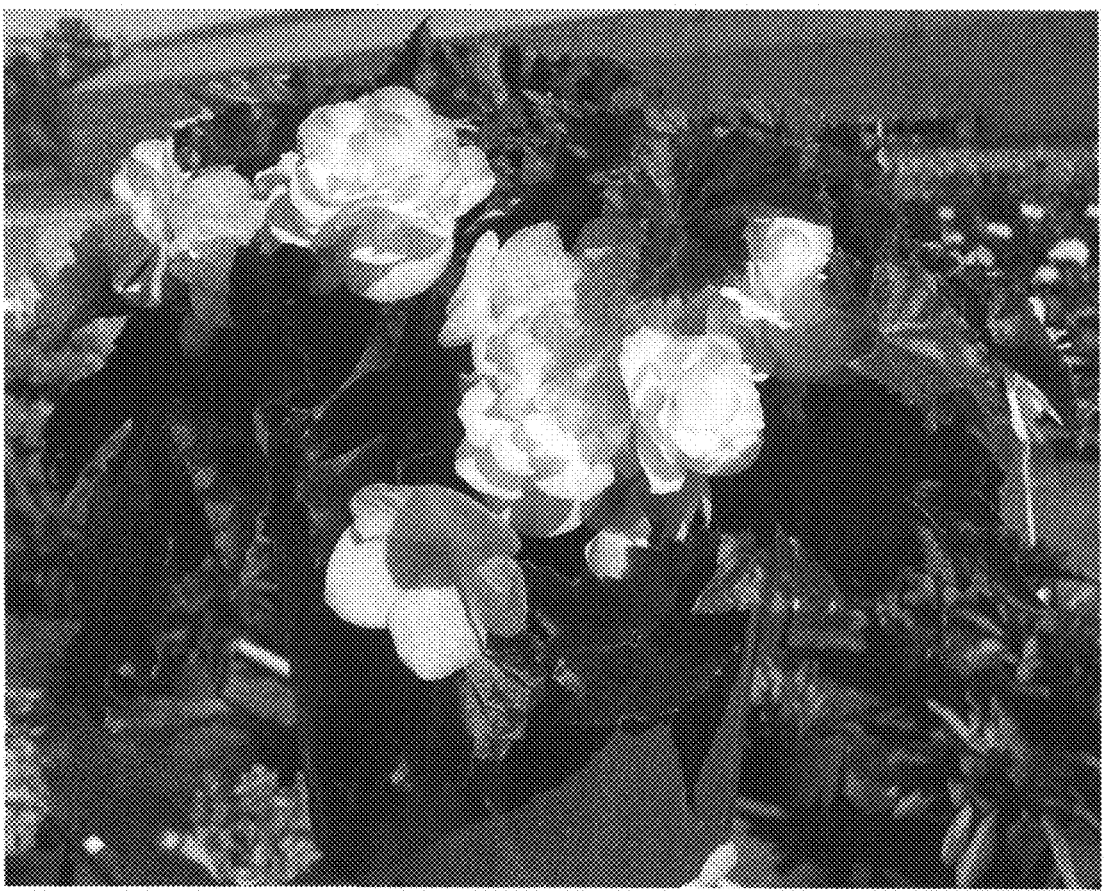
FIG. 1 depicts a whole plant view of 'Lemon Rose'.
Figure 2:
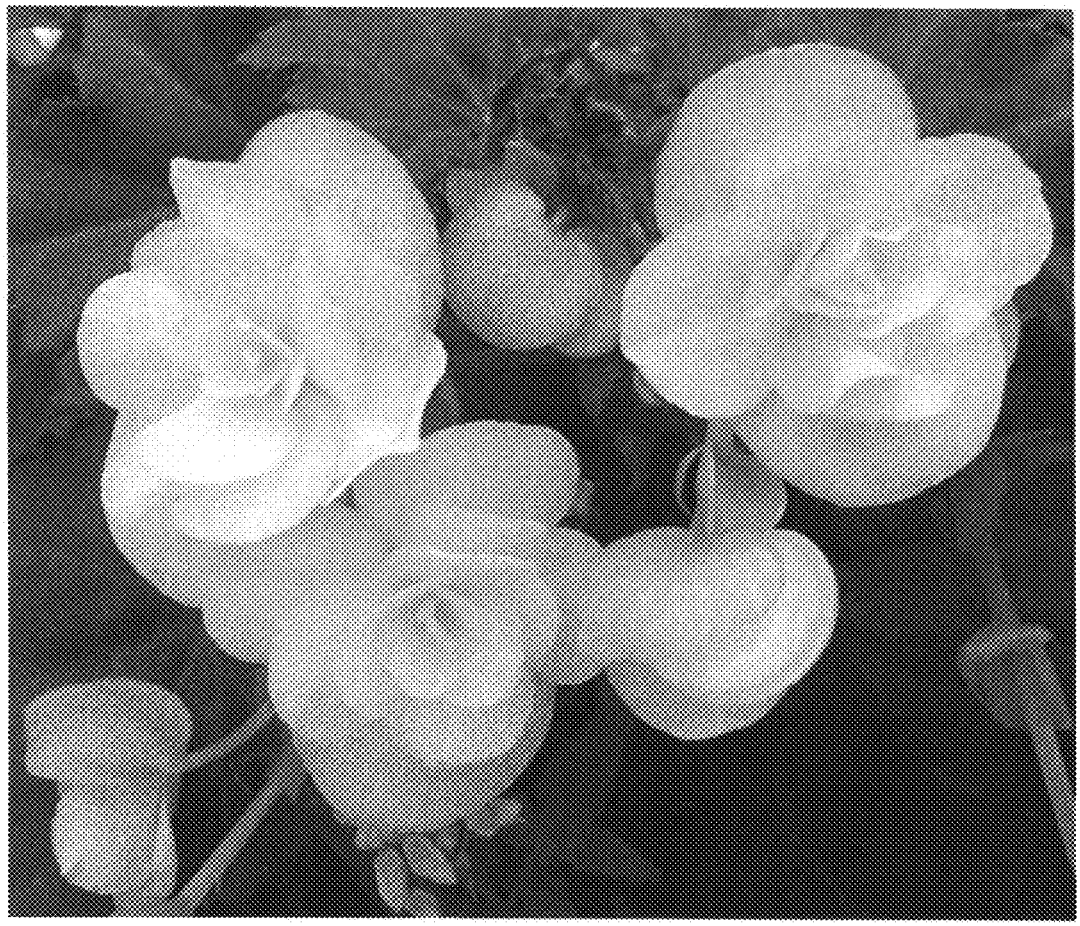
FIG. 2 depicts a close-up view of the flowers of 'Lemon Rose'.

Both photographs have been made using conventional photographic techniques and although colors may appear different from actual colors due to light reflectance, they are as accurate as possible by conventional photography.

DETAILED BOTANICAL DESCRIPTION OF THE PLANT

The following is a detailed description of plants of the new cultivar approximately 18 months in age as grown in 20 cm containers under greenhouse conditions in Whitecourt, Alberta, Canada. The color determinations are in accordance with The 2007 R.H.S. Colour Chart of The Royal Horticultural Society, London, England, except where general color terms of ordinary dictionary significance are used. The new *Begonia* variety named 'Lemon Rose' has not been observed under all possible environmental conditions. Phenotypic differences may be observed with variations in environmental, climatic, and cultural conditions, without however, any difference in genotype.

Botanical classification:

*Genus and species.*—*Begonia×tuberhybrida.*

Denomination: 'Lemon Rose'.

Commercial classification: Annual or perennial.

Plant:

*Plant uses.*—Suitable for use in patio pots, landscaping, bedding and containers.

*Cultural requirements.*—Provide good horticulture compost, 20° C. or more with a minimum of 12 hours of light needed for production in the winter months, full sun to partial shade and regular water.

*Hardiness.*—Hardy to USDA Zones 9-11.

*Parentage.*—Unnamed and unreleased seedlings from the inventor's breeding program.

*Plant description.*—Blooming seasons: Spring, summer and fall. Plant habit: Upright, bushy, freely branched. Plant form: Mounding form. Plant vigor: Vigorous. Plant propagation method: Propagated using the method of terminal stem cuttings. Production time: 10 to 12 weeks to produce a flowering plant in a 1 gallon container. Height and spread: 30 cm in height and 20 cm in spread. Diseases and pests: No susceptibility or resistance to diseases or pests has been observed. Root description: Fleshy to fibrous with no tubers produced. Time to develop roots: 10 to 14 days at 22° C. are needed to develop roots on an initial cutting.

Stem description:

*Stem size.*—Average of 20 cm in length and 6 mm in width with lateral branches about 4 mm in width.

*Stem shape.*—Round.

*Stem color.*—Ranges between 59A and 183A.

*Stem surface.*—Pubescent with sparse silver-gray hairs, length 1 mm to 2 mm; lenticels sparse, color 158A.

*Internode length.*—Average of 20 mm.

*Branching habit.*—Freely branched.

*Branching angle at emergence.*—About 45°.

*Stipules.*—Present at base of stem, triangular in shape, color 194C, length 6 mm, width 5 mm.

Foliage description:

*Leaf shape.*—Cordate, asymmetrical.

*Leaf division.*—Simple.

*Leaf base.*—Cordate.

*Leaf apex.*—Acuminate.

*Leaf venation.*—Pinnate.

*Vein color* (*adaxial surfaces*).—Ranging from 143B to 145A.

*Vein color* (*abaxial surfaces*).—Ranging from 59A to 187B.

*Leaf margins.*—Irregularly dentate; single silver-gray hair, length 1 mm to 2 mm, at tooth apex.

*Leaf attachment.*—Petiolate.

*Leaf arrangement.*—Alternate.

*Leaf surface* (*adaxial surface*).—Glossy with sparse colorless hairs.

*Leaf surface* (*abaxial surface*).—Sparsely pubescent with colorless hairs along veins.

*Leaf color* (*adaxial surface*).—Ranges between 200A and 200B except 143B to 145A adjacent to veins.

*Leaf color* (*abaxial surface*).—Juvenile foliage 59A, maturing to 187B.

*Leaf dimensions.*—Average of 7 cm in length, 4 cm in width.

*Leaf fragrance.*—None.

*Petioles.*—Ranging from 5 cm to 9 cm in length, 2 mm in width.

*Petiole surface.*—Sparsely pubescent with simple hairs, color is nearest 183D.

Inflorescence and flowers:

*General.*—'Lemon Rose' is monoecious, producing both male and female flowers on the same plant. Typically, each fully developed inflorescence consists of 4 to 5 double male flowers produced in the axils of the upper leaves which open 2 to 3 days before 3 to 4 smaller lateral double female flowers. Up to 12 flowers have been observed on a single stem (peduncle).

*Male and female flowers.*—Persistence: Self-cleaning. Type: Double. Corolla form: Funnel form, tepals unfused at base. Fragrance: Absent. Aspect: Upright and outward facing. Peduncles: Dimensions: 4.5 cm in length and 3 mm in width. Color: 179A. Surface: Smooth. Pedicel dimensions: 15 mm to 30 mm in length, 2 mm in width. Pedicel surface: Smooth, glossy. Pedicel color: 158A, except 23D when exposed to full direct bright sun. Bracts: Typically 2. Bract shape: Broad ovate. Bract apex: Obtuse. Bract length: Average 10 mm. Bract diameter: 10 mm. Bract color: 144D to 145B, margins 180A to 181C. Bract surface: Glabrous.

*Male flowers.*—(Androecium absent. Male flowers identified by position, size, lack of gynoecium). Bud shape: Flattened ovoid. Bud length: 15 mm. Bud diameter: 20 mm. Bud color: 4D, except between 36A to 39C when exposed to full direct bright sun.

*Flower dimensions.*—5 cm in length and 4.5 cm in diameter. Tepals (outer): 2 in number. Shape: Ovate. Apex: Obtuse. Base: Acuminate. Margin: Smooth, entire. Dimensions: Average of 2.5 cm in length and 2.5 cm in width. Surface (both surfaces): Glabrous and smooth. Color (both surfaces): 4D, except between 4D and 36A where surface exposed to full direct bright sun. Tepals (inner): 15 to 20 in number. Shape: Narrow elliptic. Apex: Obtuse. Base: Narrow, cuneate. Dimensions: Average of 1.5 to 2 cm in length and 1 to 1.5 cm in width, Surface (both surfaces): Glabrous and smooth. Color (inner surface): 4D, except between 8D and 36A where surface exposed to full direct bright sun. Color (outer surface): 4D, except between 4D and 36A where surface exposed to full direct bright sun. Androecium: Not observed. Pollen: Not observed.

*Female flowers*.—Bud shape: Flattened ovoid. Bud length: 15 mm. Bud diameter: 20 mm in width. Bud color: 4D, except between 36A and 39C where surface exposed to full direct bright sun. Flower dimensions: 4.5 cm in length and 4.5 cm in diameter. Tepals (quantity): 5. Shape: Ovate. Apex: Obtuse. Base: Acuminate. Margin: Smooth, entire. Dimensions: Average of 2.5 cm in length and 2.5 cm in width. Surface (both surfaces): Glabrous and smooth. Color (both surfaces): 4D, except between 4D and 39C where surface exposed to full direct bright sun. Style: Short, parted into 2-3 branches, united at base. Color between 15A and 21A. Stigma: Bifurcated, loose spiral. Ovary: Inferior, consisting of 3 carpels. Dimensions: Length: 8 mm. Diameter: 8 mm. Color (both surfaces): 145B, becoming 37C on carpel tips.

Seed: None observed to date.

I claim:

1. A new and distinct variety of *Begonia* plant named 'Lemon Rose' as described and illustrated.

* * * * *